United States Patent [19]

Lee

[11] Patent Number: 4,899,601

[45] Date of Patent: Feb. 13, 1990

[54] SAMPLE COLLECTOR

[75] Inventor: Sun Y. Lee, Arvada, Colo.

[73] Assignee: Adolph Coors Company, Golden, Colo.

[21] Appl. No.: 314,548

[22] Filed: Feb. 23, 1989

[51] Int. Cl.[4] .............................................. G01N 1/10
[52] U.S. Cl. ............................ 73/864.63; 73/863.86; 73/864.74
[58] Field of Search ........... 73/864.63, 864.74, 864.73, 73/863.86, 863.85, 863.91

[56] References Cited

U.S. PATENT DOCUMENTS 2,294,655 9/1942 Einstein ........................... 73/864.63
4,791,821 12/1988 Spencer ........................... 73/864.63

*Primary Examiner*—Hezron E. Williams
*Attorney, Agent, or Firm*—Klaas & Law

[57] ABSTRACT

A sample collector for collecting a sample of a gas-charged liquid such as a carbonated beverage from an exteriorly accessible transmission line through which the liquid is flowing. The collector comprises a cylindrical chamber for receiving and storing a liquid sample. A tube has a first end which extends inside the chamber and is positioned and configured so that liquid flowing therefrom is angularly directed against the inside wall of the chamber to create a downwardly-directed spiral flow of liquid along the inside wall. The second end of the tube has attached thereto a valve housing having a flow control valve and a forward end to which a bored needle is releasably secured. The needle bore and the tube bore are aligned and are in communication when the valve is open. The tube has a linear length and bore magnitude relationship which is conducive to inhibiting foaming of the liquid flowing therethrough for collection in the chamber, and foam production is further inhibited by the angular direction of the liquid flow against the inside wall of the chamber. To accomplish necessary tube length, the tube can be coiled on itself at a site along its length a plurality of turns to provide proper length and maintain an overall compact physical size.

13 Claims, 1 Drawing Sheet

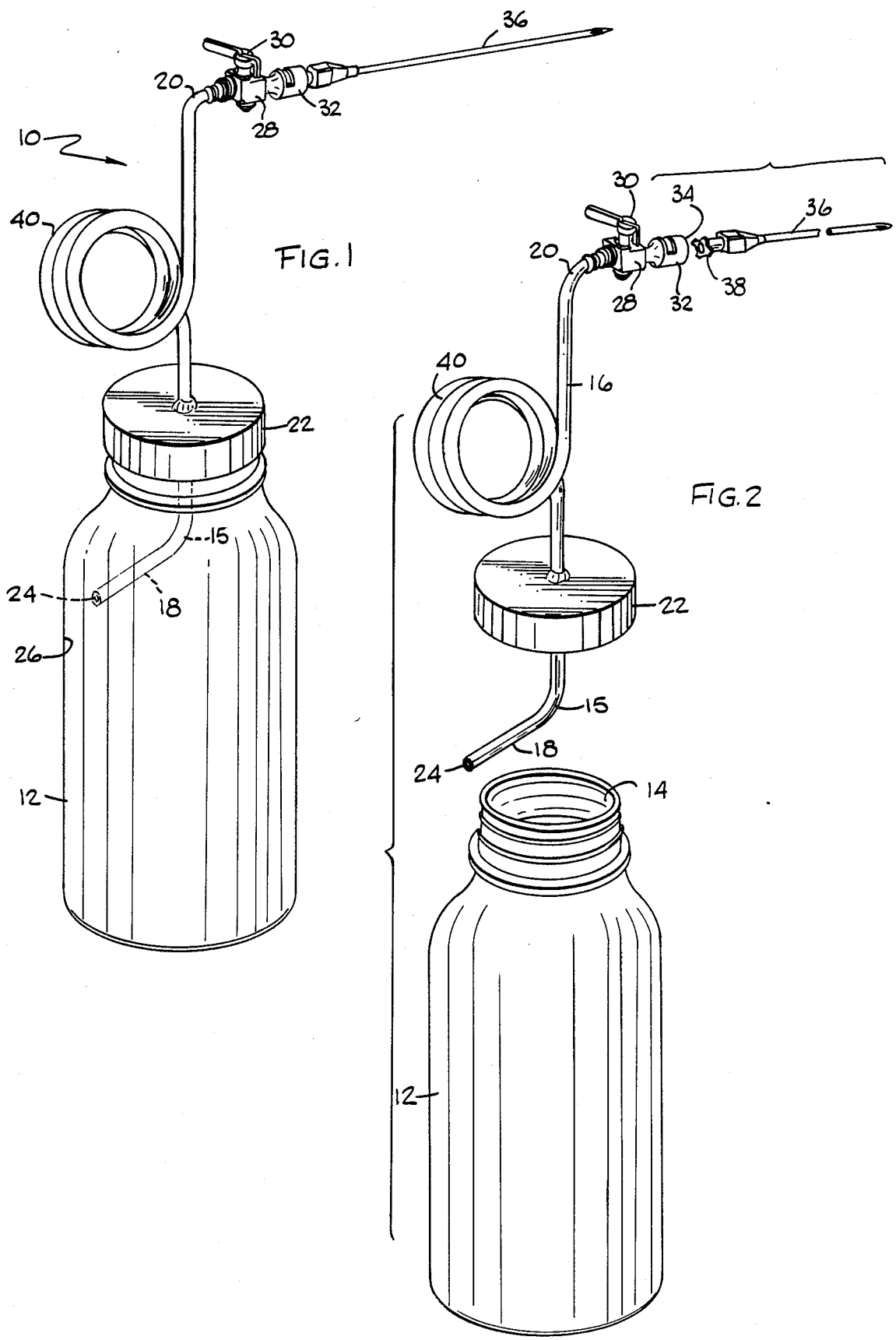

SAMPLE COLLECTOR

BACKGROUND OF THE INVENTION

This invention relates in general to a sample collector, and in particular to a sample collector for collecting a gas-charged liquid from a transmission line through which the liquid is flowing, while inhibiting the foaming of the liquid sample so collected.

In the production of gas-charged liquids such as carbonated beverages, for example, it is many times necessary to draw a sample of the liquid as it is being transported through transmission lines such as piping from a preparation site to a packaging site. Such sampling may be required to maintain quality control of the purity, taste, color, viscosity, temperature, or other characteristics of the liquid as it is being transported and packaged With respect to purity, it is especially important to be able to check for biological contamination so that contamination free conditions are maintained. In order to accommodate this need for obtaining samples, transmission lines generally have self-closing seals along their length which are permeable by a bored needle through which liquid can be withdrawn. Because the liquid is gas charged, however, employment of standard collection apparatus, which is believed to usually comprise a needle-tipped, large bore tube in straight communication with a collecting container, results in excessive foaming of the liquid so collected within the collecting container. This foaming is undesirable since it interferes with actual quantity of liquid being collectible, can be most untidy, and can require multiple re-draws in order to obtain adequate and representative samples. Additionally, excessive foaming within a sampling apparatus can itself cause contamination therein before opening because of foam leakage through any incompletely sealed escape routes.

As a result, a primary object of the present invention is to provide a sample collector wherein foaming of gas-charged liquid samples is significantly inhibited. Another object of the present invention is to provide a sample collector wherein the relationship between the length and bore magnitudes of a collection tube thereof acts to inhibit foam formation within a collecting container. Yet another object of the present invention is to provide a sample collector wherein the linear length of the tube through which collected liquid flows is increased by tube coiling upon itself at a site along its length to thereby achieve such linear length while maintaining relatively compact physical dimensions. These and other objects of the invention will become apparent throughout the description which follows.

SUMMARY OF THE INVENTION

The present invention is a sample collector for collecting a sample of a gas-charged liquid such as a carbonated beverage, for example, from a transmission line having self-closing entry means for sample collection and through which the liquid is flowing, as from a preparation site to a packaging site. The sample collector comprises a cylindrical chamber means for receiving and storing a liquid sample. A tube, having a first and a second end, is provided whereby the first end has securement means for removably securing it in a leak-proof manner within the chamber means and is positioned and configured so that liquid flowing from the first end is angularly directed against the inside wall of the chamber means to create a spiral flow of liquid along the inside wall. The second end of the tube has attached thereto a valve housing having a valve means for controlling liquid flow through the tube, and additionally having a forward end which has needle reception means for releasably securing a bored needle thereto so that the bore of the needle is in communication with the bore of the tube when the valve means is in an open position. The tube has a linear length and bore magnitude relationship which is conducive to the inhibition of foaming of the gas-charged liquid flowing therethrough into the chamber means. In a preferred embodiment, the tube is coiled upon itself at a site along its length a plurality of turns to thereby provide linear dimension while maintaining a relatively compact physical size. Finally, a bored needle is releasably secured to the forward end of the valve housing for insertion into the self-closing entry means disposed in the transmission line through which the liquid is flowing. The relationship of length and bore of the tube, and the position and configuration of the first end of the tube, which directs liquid flowing therefrom against the inside wall of the chamber means, acts to inhibit foaming of gas-charged liquid samples so collected to thereby provide superior sample collection for quality control testing and maintenance. Preferably, the entire sample collector is autoclavable and therefore reusable in its entirety, and all components thereof are non-reactive with any gas-charged liquid sample being collected.

BRIEF DESCRIPTION OF THE DRAWINGS

An illustrative and presently preferred embodiment of the invention is shown in the accompanying drawings, in which:

FIG. 1 is a perspective view of a sample collector; and

FIG. 2 is a perspective view of the sample collector of FIG. 1 in a partially disassembled configuration.

DETAILED DESCRIPTION OF A PREFERRED EMBODIMENT

Referring to FIGS. 1 and 2, a sample collector 10 for collecting a gas-charged liquid is illustrated. The collector 10 comprises a cylindrical container 12, preferably constructed of transparent or translucent autoclavable plastic, having a threaded opening 14, as a chamber means for receiving and storing gas-charged liquid. A tube 16, having a first end 18 and a second end 20 is provided, with the first end 18 thereof securedly projecting through a threaded cap 22, preferably constructed of stainless steel, and configured and positioned so that liquid flowing through the bore 24 of the tube 16 at the first end 18 is angularly directed against the inside wall 26 of the container 12 to create a downwardly-directed spiral flow, as opposed to a splash, along the inside wall 26. In the embodiment here illustrated, an angle 15 of about 50° from the vertical is chosen, and preferably is within a range between about 45° and about 55°. Depending upon the tightness of the interface between the container 12 and the cap 22, a gasket (not shown) therebetween may be required to assure leakproof securement. At the interface of the tube 16 and the cap 22, preferably stainless steel solder is applied to maintain securement in the embodiment here illustrated. At the second end 20 of the tube 16 is secured, likewise preferably by stainless steel solder, a valve housing 28 having a conventional valve means 30 for controlling liquid flow therethrough. The forward end 32 of the valve housing 28 has an interiorly threaded opening 34 as a needle reception means for releasably securing a standard bored needle 36 having lateral flanges 38 which engage the interior threads of the opening 34 to thereby align the bore of the needle 36 in communication with the bore 24 of the tube 16. In the embodiment here shown, the valve housing 28 and the needle 36, here a 16-gauge needle, are made by Beckton Dickinson Company, Rutherford, N.J., with the housing 28 having catalog no. 3153, and the needle 36 having catalog no. 1103. All Components of the embodiment here described are autoclavable, and are non-reactive with liquids being collected. Prior to use, the needle 36 is maintained with a rigid plastic cover (not shown) therearound to thereby maintain aseptic conditions.

The tube 16 is preferably constructed of stainless steel, and has a preferred linear length between about 10 inches and about 15 inches. In the embodiment here shown, the tube 16 has a linear dimension of 12 inches, yet is relatively compact in physical size as achieved by the plurality of turns 40 which act to coil the tube 16 on itself. Such coiling additionally provides a beneficial weight concentration to thereby act as a counterbalance against tipping over of the collector 10 when it is placed on a flat surface. Inside bore magnitude of the tube 16 is preferably between about 1/16 inch and ⅛ inch, with the bore in the embodiment here illustrated being 1/16 inch. The linear length magnitude of the tube to the bore magnitude thereof in the illustrated embodiment is therefore 192:1. It has been determined that a length-to-bore size relationship range of the tube 16 of from about 80:1 to about 240:1, coupled with angularly directing liquid flow against the inside wall 26 of the container 12 to create a downwardly-directed spiral flow as the liquid emerges from the first end 18 of the tube 16, are factors responsible in significantly inhibiting foam production from the gas-charged liquid collected in the container 12. In operation, and while practicing customary aseptic conditions (e.g. autoclaving the collector 10) as may be required for a particular sampling goal, an operator (1) inserts the tip of the needle 36 into a self-closing seal or other entry means of a transmission line carrying gas-charged liquid; (2) opens the valve means 30; (3) collects a liquid sample which flows into the container 12 through the bore of the needle 36, valve housing 28, and tube 16; (4) closes the valve means 30; and (5) removes the tip of the needle 36 from the transmission line entry. Should the initial amount of collected sample be inadequate due to rapid pressure equalization of the transmission line and the needle bore, removal of the needle from the entry means of the transmission line one or more times as necessary and subsequent re-insertion therein will re-establish sample flow into the container 12. The container 12 is then unscrewed from the cap 22, and the liquid can be transferred to appropriate testing and control apparatus as desired. Because foam production is inhibited in sample collection, the liquid so collected is easily handled and is of an adequate quantity as may be required for subsequent processing.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A sample collector for collecting a sample of a gas-charged liquid from a transmission line through which said liquid is flowing, with said transmission line having a self-closing entry means for insertion of a bored needle through which said liquid can flow, said sample collector comprising:
    (a) a cylindrical chamber means for receiving and storing the liquid;
    (b) a tube having a first and a second end, wherein the first end thereof has securement means for removably securing it in a leak-proof manner within the chamber means and is positioned and configured so that liquid flowing from said first end is angularly directed against the inside wall of the chamber means to create a downwardly-directed spiral flow along said inside wall, and wherein the second end thereof has attached thereto a value housing having valve means for controlling liquid flow through the tube, said valve housing additionally having a forward end having needle reception means for releasably securing a bored needle thereto so that the bore of the needle is in communication with the bore of the tube when the valve means is in an open position, with said tube having a relationship between linear length and bore magnitudes conducive to the inhibition of foaming of the gas-charged liquid flowing therethrough into the chamber means; and
    (c) a bored needle releasably secured to the forward end of the valve housing.

2. A sample collector as claimed in claim 1 wherein the chamber means comprises a container having a threaded opening, and the securement means for removably securing the first end of the tube within the chamber means comprises a threaded cap engageable with the threaded opening of the container and through which the first end of the tube is fixedly secured for projection into said container when the container opening and cap are threadably engaged.

3. A sample collector as claimed in claim 2 wherein the tube is coiled upon itself at a site along its length a plurality of turns.

4. A sample collector as claimed in claim 3 wherein the relationship of the linear length magnitude of the tube to the bore magnitude thereof is from about 80:1 to about 240:1.

5. A sample collector as claimed in claim 4 wherein the relationship of the linear length magnitude of the tube to the bore magnitude thereof is from about 175:1 to about 215:1.

6. A sample colector as claimed in claim 4 wherein the chamber means, tube, valve means, valve housing, and bored needle are constructed of material which is nonreactive with the gas-charged liquid.

7. A sample collector as claimed in claim 6 wherein the chamber means, tube, valve means, valve housing and bored needle are autoclavable.

8. A sample collector as claimed in claim 7 wherein the tube, valve means, valve housing, and bored needle are constructed of stainless steel.

9. A sample collector as claimed in claim 1 wherein the relationship of the linear length magnitude of the tube to the bore magnitude thereof is from about 80:1 to about 240:1.

10. A sample collector as claimed in claim 1 wherein the chamber means, tube, valve means, valve housing, and bored needle are constructed of material which is nonreactive with the gas-charged liquid.

11. A sample collector as claimed in claim 10 wherein the chamber means, tube, valve means, valve housing, and bored needle are autoclavable.

12. A sample collector as claimed in claim 11 wherein the tube, valve means, valve housing, and bored needle are constructed of stainless steel.

13. A sample collector as claimed in claim 1 wherein the tube is coiled upon itself at a site along its length of plurality of turns.

* * * * *